United States Patent [19]

McVay et al.

[11] Patent Number: 4,724,840
[45] Date of Patent: Feb. 16, 1988

[54] SURGICAL FASTENER APPLIER WITH ROTATABLE FRONT HOUSING AND LATERALLY EXTENDING CURVED NEEDLE FOR GUIDING A FLEXIBLE PUSHER

[75] Inventors: William P. McVay, Clearwater, Fla.; Szabolcs M. Vigh, Woodbridge, N.J.; Glen C. Dorband, Somerville, N.J.; Donald M. Golden, Cherry Hill, N.J.

[73] Assignee: Ethicon, Inc., Somerville, N.J.

[21] Appl. No.: 345,280

[22] Filed: Feb. 3, 1982

[51] Int. Cl.[4] .............................................. A61B 17/04
[52] U.S. Cl. ................................. 128/334 R; 128/330; 128/339
[58] Field of Search ............. 227/DIG. 1; 128/334 C, 128/335, 337, 339–340, 325–326; 29/243.56; 72/410; 604/57–64

[56] References Cited

U.S. PATENT DOCUMENTS

| | | | |
|---|---|---|---|
| 2,396,179 | 3/1946 | Karle | 128/340 |
| 2,439,383 | 4/1948 | Erickson | 128/340 |
| 2,883,984 | 4/1959 | Candido | 604/61 |
| 4,049,177 | 9/1977 | Bussard | 227/DIG. 1 |
| 4,224,947 | 9/1980 | Fukuda | 128/340 |

Primary Examiner—C. Fred Rosenbaum
Assistant Examiner—Gene B. Kartchner
Attorney, Agent, or Firm—Robert L. Minier

[57] ABSTRACT

A device is provided for applying flexible fasteners to tissue to close a wound or incision. The device has a front housing mounted for rotation relative to a rear housing. A needle projects laterally from the front housing. The needle is curved, hollow, and slotted for receiving a portion of a fastener. The device has a flexible pusher member and means for moving the flexible pusher member into the hollow needle to eject a fastener from the needle and into the tissue.

10 Claims, 14 Drawing Figures

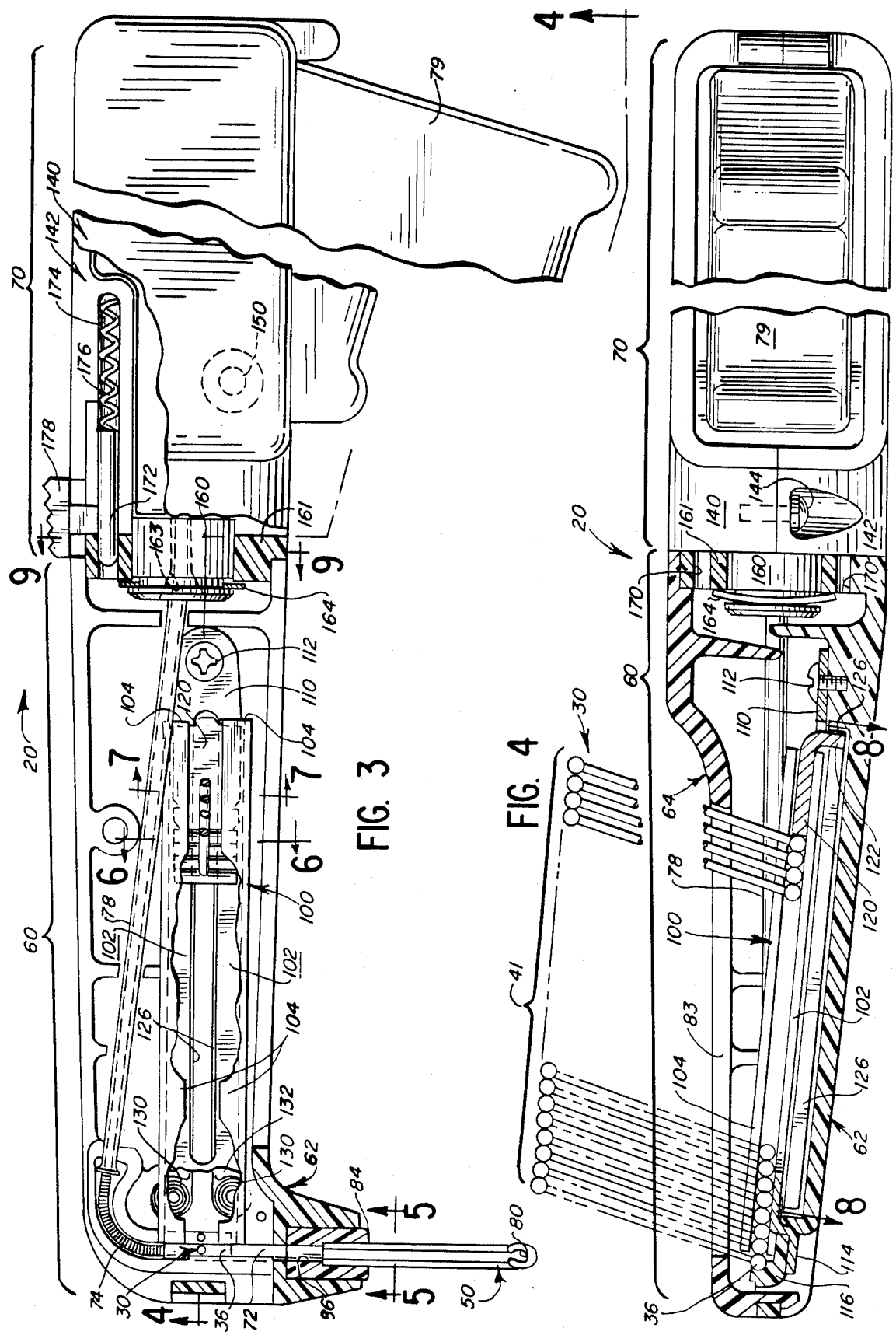

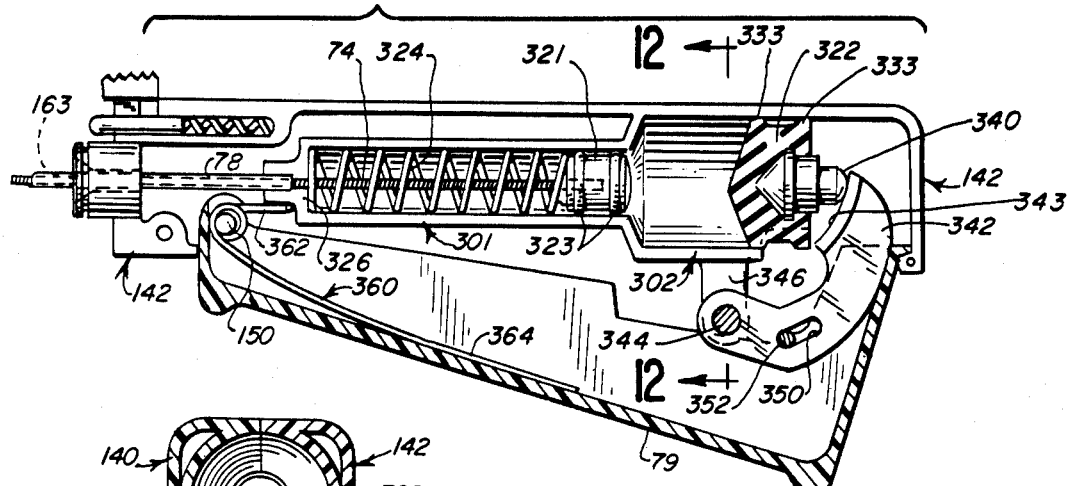
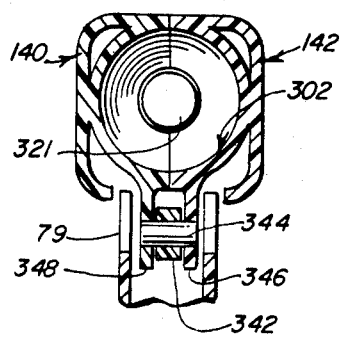
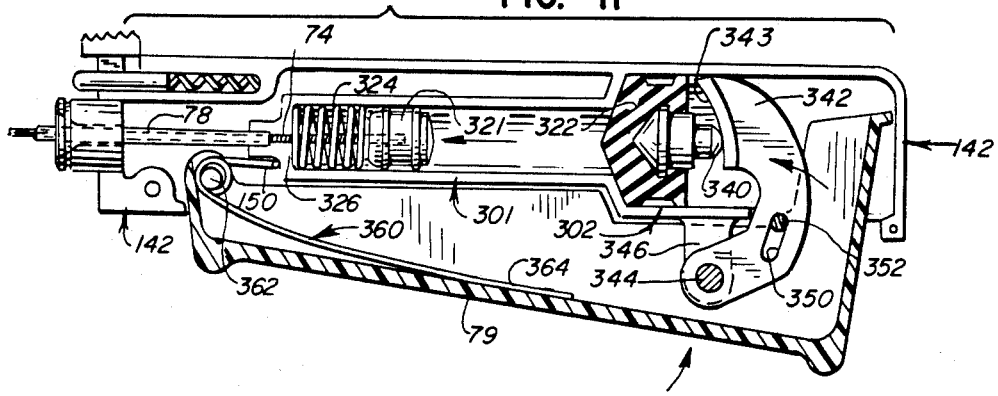

SURGICAL FASTENER APPLIER WITH ROTATABLE FRONT HOUSING AND LATERALLY EXTENDING CURVED NEEDLE FOR GUIDING A FLEXIBLE PUSHER

TECHNICAL FIELD

This invention relates to surgical instruments and more particularly to an instrument for applying a fastener through tissue to close a wound or incision.

BACKGROUND OF THE INVENTION

A method has been proposed for using an instrument or device for closing wounds or surgical incisions in mammalian tissue with fasteners made from flexible and resilient biocompatible material which may be either absorbable or nonabsorbable in body tissue. One such type of device for applying such a fastener to tissue is generally disclosed in U.S. Pat. No. 4,006,747.

The device disclosed in U.S. Pat. No. 4,006,747 generally includes (1) a slotted, hollow, straight, needle adapted to carry a portion of the fastener, (2) a rigid plunger for pushing the fastener along the straight needle and into the tissue, and (3) a mechanism for moving the plunger into the needle and for then withdrawing the plunger from the needle.

Other devices of the type disclosed in U.S. Pat. No. 4,006,747 suitable for use in applying various types of fasteners are disclosed in U.S. Pat. Nos. 3,470,834, 3,103,666, 2,069,878, 3,494,004, 3,399,432, 3,518,729, and U.S. Pat. No. 313,418.

Other devices for applying fasteners in non-surgical situations are disclosed in U.S. Pat. Nos. 3,209,422 and 3,733,657.

Prior to the disclosure in U.S. Pat. No. 4,006,747 of the method for applying a fastener simultaneously through a needle and tissue, procedures for the manual application of sutures or fasteners through tissue with needles or needle-like elements were known. Examples of such sutures and needles are disclosed in U.S. Pat. Nos. 3,636,956, and 3,716,058.

The fastener applying device disclosed in the above-discussed U.S. Pat. No. 4,006,747 has a generally elongate housing with the straight needle projecting from the front end of the housing generally parallel to the longitudinal axis of the housing.

The inventors of the present invention have determined that it would be desirable to provide an improved housing and needle configuration that would permit the surgeon to use a hand movement substantially similar to that used when applying conventional sutures with conventional suture needles. This would be desirable since most surgeons have developed, and have become accustomed to, such hand movement when applying conventional sutures. Therefore, the adoption and use of such an improved fastener applier device by surgeons would be more readily facilitated.

The inventors of the present invention have also determined that it would be desirable to provide an improved housing structure that would enable the surgeon to conveniently maintain the needle on the front portion of the instrument in a desired orientation relative to the rear portion of the instrument.

The inventors of the present invention have also determined that it would be advantageous to provide an improved needle shape and configuration that would be specifically adapted for piercing tissue and that would facilitate the picking up and holding of tissue as the tissue is pierced with the needle.

It would be also beneficial if the improved fastener applier device could be made from relatively inexpensive materials so that the device, after being initially provided to the surgeon in a sterile package, can be disposed of after one use. With such a disposable device, it would be desirable to provide a design that would facilitate fabrication of the device from non-toxic materials that would have little or no deleterious effects on the environment as a result of proper disposal of the device after use.

SUMMARY OF THE INVENTION

The present invention provides a novel fastener applier device for surgical procedures. The fastener applier device of the present invention is adapted to apply a fastener of the type comprising a filament member terminated on at least one end by an anchoring means. The other end may also have an anchoring means.

The fastener is applied by the fastener applier device to remain in the tissue with the filament member transversing the wound or incision through the tissue to maintain the tissue in approximation at the wound or incision.

The device has a front housing and a rear housing that are mounted together to permit relative rotation of the housings about a common longitudinal axis. In the preferred embodiment of the invention, a mechanism is provided for releasably latching the front and rear housings at selected relative azimuthal orientations.

A hollow needle projects laterally outwardly away from the housing in a plane generally normal to the axis of relative rotation of the front and rear housings. The needle has a distal end adopted for piercing tissue and is curved along at least a portion of its length in a circular arc to facilitate the picking up and holding of the tissue as the tissue is pierced with the needle. The needle has an internal passage and a slot extending along its length through which the fastener is applied.

The needle receives an anchoring means of the fastener. The passage and slot in the needle extend along the length of the needle from an entrance aperture to a discharge aperture at the distal end of the needle. The needle slot communicates with the passage along the length of the needle from the entrance aperture to the discharge aperture. The slot is adapted to receive a portion of the fastener filament member.

The device includes a flexible pusher member, actuated by a mechanism and handle carried in the rear housing, for pushing the fastener along the needle to eject the fastener from the needle into the tissue.

Preferably, the device also includes a fastener magazine in the front housing for retaining and guiding a plurality of fasteners in side-by-side, unconnected, relationship. The magazine further includes a spring mechanism for biasing the plurality of fasteners toward a dispensing channel or region in alignment with the entrance aperture of the needle passage.

The length of the pusher member and the movement stroke effected by the actuating mechanism is selected so that the pusher member can be reciprocated between (1) a retracted position spaced inwardly from the discharge aperture of the needle to permit admission of a fastener into the needle (preferably as fed by the fastener magazine) and (2) an extended position outwardly along the needle relative to the retracted position wherein the fastener is ejected from the discharge aperture of the needle by the pusher member.

The housing rotation feature described above permits the needle, which extends from the front housing, to be positioned at a desired orientation relative to the rear housing (by which the surgeon holds the device) during operation of the device.

The present invention resides in the combination, construction, arrangement, and disposition of various component parts and elements incorporated in the device in accordance with the principles of this invention. The present invention will be better understood and important features other than those specifically enumerated above will become apparent when consideration is given to the following details and description which, when taken in conjunction with the annexed drawings, describes, discloses, illustrates, and shows preferred embodiments of the present invention and what is present considered and believed to be the best mode of practicing the principles of the invention. Other embodiments and modifications may be suggested to those having the benefit of the teachings herein, and such other embodiments and modifications are intended to be reserved, especially as they fall within the scope and spirit of the subjoined claims.

BRIEF DESCRIPTION OF THE DRAWINGS

In the accompanying drawings forming part of the specification, and in which like numerals are employed to designate like parts throughout the same.

FIG. 3 is an enlarged, partial cross-sectional view taken generally along the plane 3—3 in FIG. 1 but modified to show the device in the unactuated or released mode;

FIG. 4 is a partial cross-sectional view taken generally along the planes 4—4 in FIG. 3;

FIG. 10 is a fragmentary, cross-sectional view similar to FIG. 3 but showing only the rear portion of the fastener applier device, which rear portion contains the handle means and actuating means shown in the unactuated or released position;

FIG. 11 is a view similar to FIG. 10 but showing the handle means and actuating means in the moved or actuated position; and FIG. 12 is a fragmentary, cross-sectional view taken generally along the plane 12—12 in FIG. 10.

DESCRIPTION OF THE PREFERRED EMBODIMENT

This invention may be used in many different forms. This specification and the accompanying drawings disclose a specific form as an example of the use of the invention. The invention is not intended to be limited to the embodiment illustrated, and the scope of the invention will be pointed out in the appended claims.

The precise shapes and sizes of the components herein described are not essential to the invention unless otherwise indicated.

For ease of description, the device of this invention will be described in an orientation as illustrated in the figures and terms such as upper, lower, horizontal, etc., will be used with reference to this orientation. It will be understood, however, that the device of this invention may be manufactured, stored, transported, used, and sold in an orientation other than the position described.

In the following description, reference is made to the industry standards of the American Iron and Steel Institute, 1000 16th Street, N.W., Washington, D.C. U.S.A. 20036. These standards will be designated by the common initial letters "AISI" followed by a suffix comprising additional alphanumeric characters and the standards are understood to be those in effect as of Aug. 1, 1981.

For ease of understanding the present invention, the invention is illustrated in two preferred embodiments each comprising a hand-held, hand-operated device for closing a wound or incision in tissue with a particular type of fastener. Before describing in detail the various components of the fastener applier device, the fastener and the general method of applying the fastener with the device will first be described. This will be followed by a detailed description of the elements comprising the fastener applying device.

THE FASTENER

Figure 1:
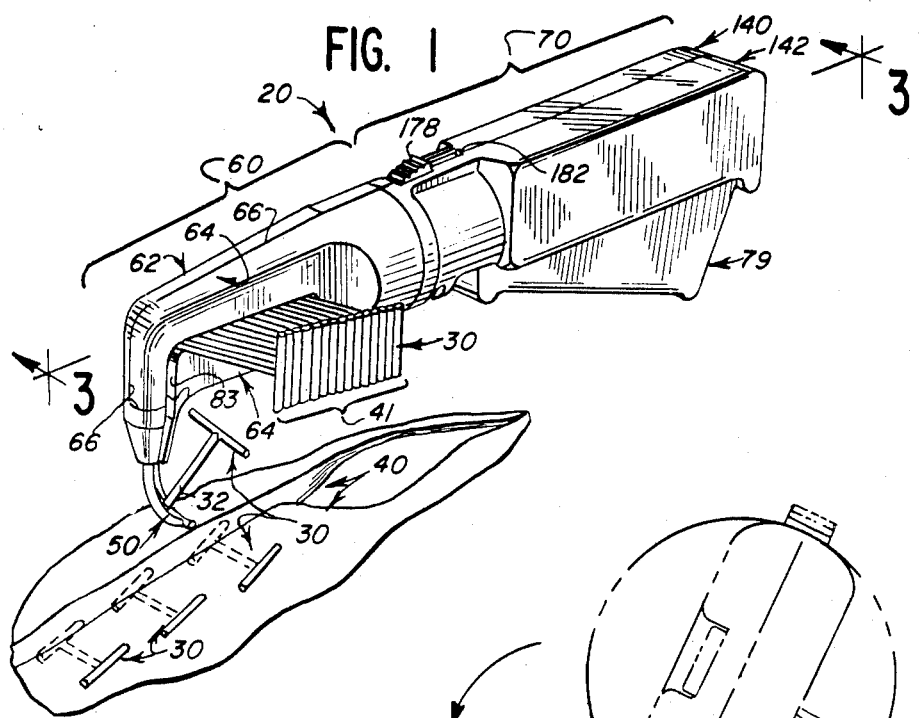
FIG. 1 is a perspective view of a first embodiment of a hand-held surgical fastener applier device or instrument shown being used to close an incision in tissue in a surgical procedure.

FIG. 1 illustrates a method of applying, with a fastener applier device 20 of the present invention, a plurality of fasteners 30 to skin or other tissue 40 in a surgical procedure.

The fastener 30 is identical to the flexible fastener disclosed in the U.S. Pat. No. 4,006,747 and reference is directed thereto for a complete description of such a fastener. Briefly, with reference to FIG. 2c of the drawings annexed hereto, the fastener 30 includes a filament member 32 terminated at one end by first anchoring means or rod-shaped head 36 and at the other end by an identical second anchoring means or rod-shaped head 34.

The fastener 30 is conveniently H-shaped and constructed of a flexible and resilient biocompatible material which may be either absorbable or non-absorbable in body tissue. As disclosed in detail in the above-referenced U.S. Pat. No. 4,006,747, the fastener 30 may be constructed of any of the wide variety of materials or combinations of materials. For example, materials such as nylon and polypropylene can be used to mold nonabsorbable fasteners 30 with good results. Also, copolymers of glycolide and lactide can also be used with good results and have the additional advantage of being absorbable in tissue and thus are particularly well suited for internal use in applications where long-term maintenance of wound support is not required.

As best illustrated in FIG. 1, a series of fasteners 30 are typically placed in close proximity along the length of the wound or incision to effectively close the wound or incision and enable natural healing to proceed. Nonabsorbable fasteners are removed from the tissue closures by snipping off one head and withdrawing the fastener with the opposite head.

METHOD OF APPLYING THE FASTENER

Figure 2A:
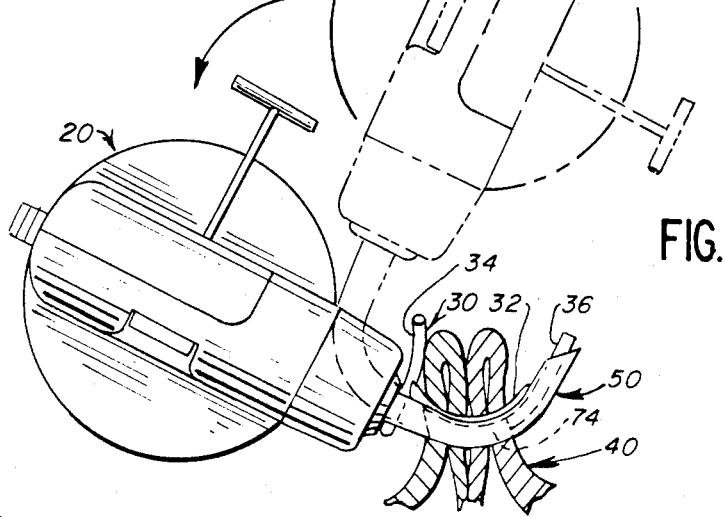
FIG. 2a is an end view of the fastener applier device of FIG. 1 and a fragmentary, partial cross-sectional view of the tissue with the device shown in dashed line in a first position as the needle pierces the tissue and with the device shown in solid line in a moved position while placing a fastener across the incision.
Figure 2B:
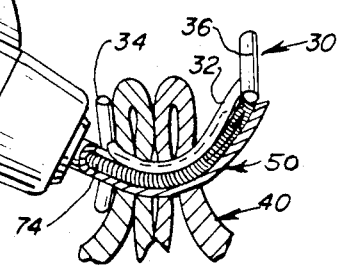
FIG. 2b is a view similar to FIG. 2a but showing a stage in the surgical procedure that is later than that illustrated in FIG. 2a and showing the needle in partial cross-section.
Figure 2C:
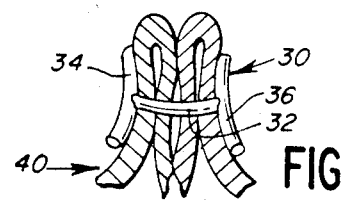
FIG. 2c is a fragmentary, cross-sectional view of the incision after the fastener applier device has been removed so as to leave the fastener in place across the incision.

As best illustrated in FIG. 2c, and as more fully described in the above referenced U.S. Pat. No. 4,006,747, the fastener 30 is used to close a wound or incision by first folding over the tissue 40 on each side of the wound or incision and then approximating the folded over portions. Next, with the folded tissue held, as by grasping it with forceps, the flexible fastener 30 is temporarily bent or deformed and inserted through the skin on both the sides of the wound or incision. This can be effected with a fastener applying device, such as the device 20 illustrated in FIGS. 1–2b, in the general manner disclosed in the above-referenced U.S. Pat. No. 4,006,747.

Specifically, the device 20 is provided with means for holding a plurality of fasteners 30 in an aligned row 41 as best illustrated in FIG. 1. The device 20 includes a hollow needle 50 adapted for receiving one rod-shaped head of the fastener 30 as best illustrated in FIG. 1. The needle 50 also has a longitudinally extending slot through which the filament 32 of the fastener projects. The device 20 is adapted to feed one fastener 30 at a time into the hollow, slotted needle 50 and to push the fastener along the needle.

In the above-discussed U.S. patents relating to fastener devices, and especially in the U.S. Pat. No. 4,006,747, the fastener applier device has a straight needle in which is slidably disposed a rigid pusher rod. In contrast, the present invention teaches, inter alia, that the needle 50 is curved in a circular arc for at least a portion of its length and projects laterally outwardly from the device housing in a plane normal to the length of the device. A flexible pusher member 74 is provided to be slidably received within the curved needle 50 to eject the fasteners.

As best illustrated in FIG. 2a, the needle 50 is passed into the approximated and folded tissue 40 from a point on one side of the wound and on through the tissue until the tip of the needle 50 exits the tissue on the opposite side of the wound.

The path of the needle 50 through the tissue is not unlike that followed in conventional suturing. While closing a wound by conventional suturing, the needle and a length of attached suture are passed completely through the tissue. The hollow needle in the present case is inserted only far enough to penetrate through the tissue to form an open communication with both sides of the wound.

As best illustrated in FIGS. 2a and 2b, the flexible pusher member 74 (visible in FIG. 2b) is adapted to reciprocate within the curved, hollow needle 50 and to engage and push an end of the fastener's rod-shaped head 36 through the hollow needle until the fastener is discharged from the tip of the needle 50 on the far side of the wound. Then the needle 50 is withdrawn from the tissue while the fastener 30 is restrained in the tissue 40 by the head 36 on the far side of the wound. The fastener is thus left in the tissue 40 with the filament 32 of the fastener 30 traversing the wound along the path created by the needle 50 and with the two anchoring means (the heads 34 and 36) engaging and restraining the surface of the tissue 40 on either side of the wound or incision.

The needle 50 is curved along a circular arc and also projects downwardly and outwardly to one side of the fastener applier device 20 as illustrated in FIG. 1. The needle 50 projects laterally from the device 20 in a plane generally normal to the longitudinal axis of the device (which longitudinal axis is the axis about which the front portion of the device can be rotated relative to the rear portion as will be explained in detail hereinafter).

The inventors of the present invention have found that certain advantages can be realized with such a design. Specifically, the use of a needle having this type of orientation on the device 20 permits the surgeon to use a hand movement that is substantially similar to that used when applying conventional sutures with conventional suture needles. This is desirable since most surgeons have developed, and have become accustomed to, such hand movement when applying conventional sutures. Therefore, the adoption and use of the fastener applier device 20 of the present invention by a surgeon is more readily facilitated.

FIGS. 1–2c illustrate the tissue or skin 40 being folded over once at each side of the wound. It is to be realized that such a fold is not necessary when closing a wound or incision with the fastener 30 as installed by the fastener applier device 20 of the present invention. Specifically, reference is directed to FIGS. 2 and 4 of the above-discussed U.S. Pat. No. 4,006,747 for illustrations of the use of a fastener identical to the fastener 30 disclosed herein but wherein the tissue on each side of the wound is not folded over.

MAGAZINE AND NEEDLE STRUCTURE

As best illustrated in FIG. 1, the device 20 has a generally elongate housing having a front or magazine portion 60 that contains the fastener row 41 and needle 50 and having a rear portion 70 that houses the actuating mechanism. A handle, trigger, or handle means 79 extends from the rear housing portion 70.

The first or front end portion 60 will next be described in detail with reference to FIGS. 1 and 3–5. With reference to FIG. 1, the front end portion 60 of the device preferably comprises two molded portions or pieces, piece 62 and piece 64. Each piece is preferably molded from a suitable material. For example, the pieces 62 and 64 may be molded from a polycarbonate resin such as that sold in the United States of America under the trademark or trade name Merlon M40 F by the Mobay Chemical Corporation.

Pieces 62 and 64 are mated together about a parting plane 66 (seen in FIG. 1 as the line running the length of the device 20). The pieces 62 and 64 are joined together by suitable means such as screws, adhesive, or other bonding means (not illustrated). In FIG. 3, the first piece 62 is viewed along its parting plane and is seen to define an arcuate channel 72 at the front end in which the flexible pusher member 74 is slidably disposed. The flexible pusher member 74 is preferably constructed from AISI 316 L Series stainless steel 30 gauge wire wound in a helical configuration having a radius slightly less than the radius of the arcuate channel 72.

The flexible pusher member 74 extends rearwardly in the device 20 from the front end of the housing magazine portion 60 through a hollow tube 78 into the rear portion 70 and is operatively engaged with the actuating means within the housing rear portion 70 as will be explained in detail hereinafter.

As best illustrated in FIGS. 1 and 4, the piece 64 of the housing front end portion 60 defines an L-shaped slot 83, the base leg portion of which L-shaped slot 83 is in registry with the arcuate channel 72 of the mating housing piece 62. The other leg of the L-shaped slot 83 receives the row 41 of fasteners 30.

Figure 5:
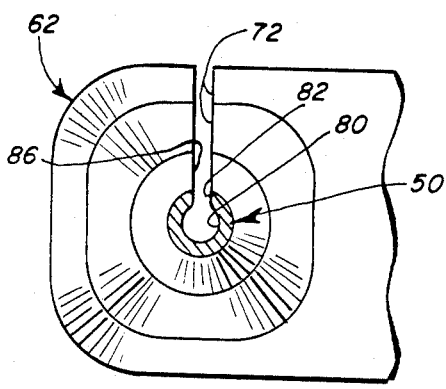
FIG. 5 is a cross-sectional view taken generally along the plane 5—5 in FIG. 3.

The front end of the housing piece 62 has a generally conical configuration as best illustrated in FIGS. 1 and 5 and carries a needle holder insert 84 as best illustrated in FIG. 3. The needle holder insert 84 has a generally cylindrical configuration with a slot 86 in registry with the channel 72 of the housing piece 62.

The needle 50 is secured by a suitable means within the needle holder insert 84 and projects from the distal end thereof as best illustrated in FIGS. 3 and 5. The needle 50 is hollow and extends outwardly away from the housing piece 62 in a circular arc and in a plane substantially normal to the longitudinal axis of the device 20. Although substantially the entire length of the needle that extends from the front housing piece 62 has a circular arc curvature, the portion of the needle mounted within the housing piece 62 is straight. The distal end of the needle 50 is preferably angled or sharpened (as best illustrated in FIG. 2a) to facilitate the piercing of tissue.

The needle 50 defines a passage 80 as best illustrated in FIG. 5. The passage 80 extends along the length of the needle 50 from the entrance aperture of the needle within the needle holder insert 84 to the discharge aperture at the distal end of the needle 50. The needle 50 also defines a slot 82 along its length as best illustrated in FIG. 5. The slot 82 is coextensive with the passage 80 and therefore extends from the entrance aperture of the needle 50 within the needle holder insert 84 to the discharge aperture at the distal end of the needle 50. The slot 82 communicates with the passage 80 along the entire length of the needle 50. The passage 80 is thus open through the slot 82 inwardly toward the center of curvature of the needle. The passage 80 of the needle 50 is adapted to receive one of the fastener anchoring means or rod-shaped heads (head 36 in FIG. 2a). The slot 82 of the needle 50 is adapted to receive a portion of the filament 32 of the fastener 30.

In a preferred form of the invention illustrated, the needle 50 and the needle holder insert 84 are both preferably fabricated from a suitable metal, such as AISI 420 stainless steel. Preferably then the insert 84 and needle 50 are welded together to form an integral assembly which is then suitably secured within the conical portion of the housing piece 62.

Figure 6:
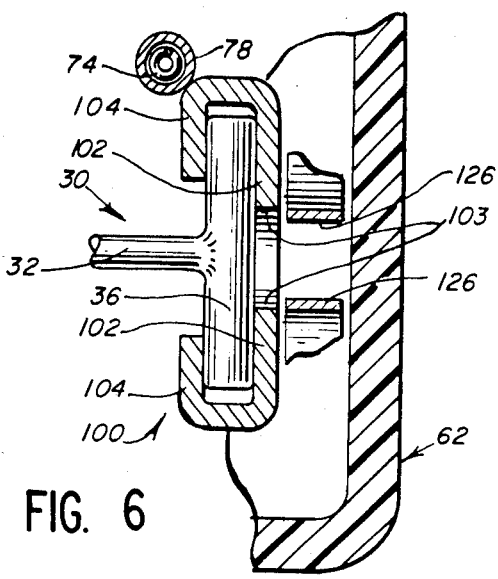
FIG. 6 is a fragmentary, enlarged, cross-sectional view taken generally along the plane 6—6 in FIG. 3.

As best illustrated in FIGS. 3 and 4, the front portion 60 of the fastener applier device 20 also includes a magazine 100 for holding a plurality of fasteners 30 in the row 41 and for feeding the fasteners 30 seriatim into the channel 72 defined in the front housing piece 62. Specifically, as best illustrated in FIGS. 3, 4, and 6, the magazine 100 includes a base member 102 defining a slot 103 and having a pair of angled retainer flanges 104 adapted to receive the fasteners 30. Specifically, the anchor means or rod-shaped head 36 of each fastener 30 is slidably received within the flanges 104 and on top of the slotted member 102. The fastener filament member 32 extends out of the magazine through the space defined between the flanges 104.

The magazine 100 is mounted within the housing portion 62 as best illustrated in FIGS. 3 and 4. Specifically, the rear end of the magazine 100 has a rearwardly extending tab 110 by which the magazine 100 is secured with a screw 112 to the housing portion 62. At the front end of the magazine 100, the magazine 100 has an off-set but forwardly extending tab 114 which is retained under a cross wall 116 of the housing portion 62.

Slidably disposed within the magazine 100 on top of the bottom member 102 is a feeder member 120 (FIGS. 4 and 7) which has a downwardly depending tab 122 disposed through the central slot 103 of the magazine bottom member 102.

Figure 7:
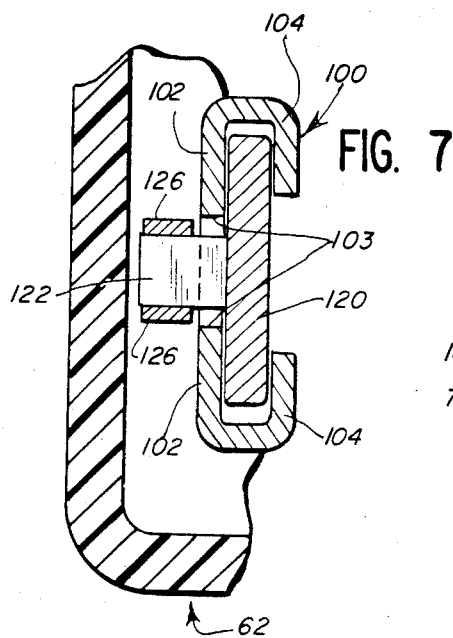
FIG. 7 is a fragmentary, enlarged, cross-sectional view taken generally along the plane 7—7 in FIG. 3.
Figure 8:
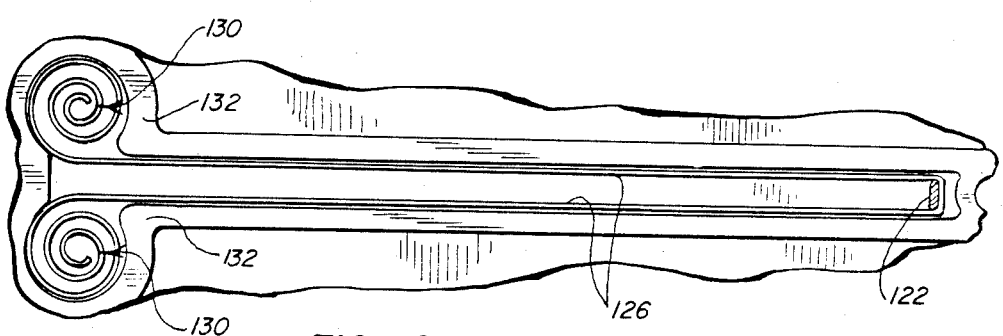
FIG. 8 is a fragmentary, enlarged, cross-sectional view taken generally along the plane 8—8 in FIG. 4.

The downwardly depending tab 122 of the feeder member 120 is biased forwardly with a band spring 126 as best illustrated in FIG. 4. As best illustrated in FIGS. 3, 7, and 8, the band spring has two oppositely coiled portions 130 which are disposed within a retainer or guide wall 132. The central portion of the band spring 126 is pulled outwardly from the coiled portions 130 and extends underneath and along the length of the magazine 100 to the feeder member tab 122 with which it is engaged. Thus, the feeder member 120 is continuously biased forwardly to push the fasteners 30 toward the channel 72 defined in the housing piece 62.

The guide tube 78, the arcuate channel 72 in the housing piece 62, and the channel 86 in the needle holder insert 84 all function as a guide means in the housing that serves to guide the movement of the flexible pusher member 74 into alignment with the entrance aperture and a passage 80 of the needle 50. Further, that portion of the channel 72 in the housing piece 62 immediately adjacent the front end of the magazine 100 can be regarded as defining a "fastener dispensing region" aligned with the entrance aperture of the needle 50 for accommodating admission of the fastener rod-shaped head 36 in registry or alignment with the entrance aperture and passage 80 (FIG. 5) of the needle 50.

As best illustrated in FIGS. 3 and 4, the width of the channel 72 in the housing portion 62 has a configuration and dimensions sufficient to accommodate the rod-shaped end of just one of the fasteners 30 at the front end of the magazine 100. The head 36 of the fastener is fed from the magazine 100 into the channel 72 just forward of the flexible pusher member 74 when the flexible pusher member 74 is in a fully retracted position. The channel 72 of the housing piece 62 thus serves to guide and align the flexible pusher member 74 and the rod-shaped head 36 of the fastener with the passage 80 of the needle 50. When the flexible member 74 is moved forwardly toward the needle 50 by suitable actuating means (described in detail hereinafter), the rod-shaped head 36 of the fastener 30 travels along the channel 72 of the housing piece 62, along the channel 86 of the needle holder insert 84, and finally through the needle 50. The flexible pusher member 74 is moved forwardly until its leading end pushes the fastener rod-shaped head 36 out of the needle passage 80 (as illustrated in detail in FIG. 2b).

After the rod-shaped head 36 of the fastener has been ejected from the needle discharge aperture, the flexible pusher member 74 is retracted back to the position illustrated in FIG. 3 (by means described in detail hereinafter). As long as the flexible pusher member 74 extends beyond the front of the magazine 100, the next fastener 30 in the magazine 100 is prevented from being fed from the magazine to the channel 72 in the housing piece 62. However, as soon as the flexible pusher member 74 has returned to a point just behind the magazine 100 as illustrated in FIG. 3, the next fastener 30 is urged forwardly into the channel 72 of the housing piece 62. Thus, the fastener applier device 20 is ready to apply the next fastener.

The magazine 100 is uniquely designed to prevent actuation of the instrument after all of the fasteners 30 have been ejected and when the magazine 100 is thus empty. Specifically, with continued reference to FIGS. 3 and 4, it can be seen that the forward or distal end portion of the feeder member 120 will project into the channel 72 after the last fastener has been ejected and after the flexible pusher member 74 has been fully retracted from the fastener dispensing region in front of the magazine 100. The fastener feeder member 120 will be maintained in this position at the forward end of the magazine by the band spring 126. Consequently, any attempt to move the flexible pusher member 74 forward from the fully retracted position illustrated in FIG. 3 will fail since the distal end of the flexible pusher member 74 will necessarily impinge against the end of the fastener feeder member 120 projecting into the channel 72. This prevents the handle 79 from being actuated and thus serves as an indication that all of the fasteners have been ejected from the instrument.

REAR HOUSING AND ACTUATING HANDLE MOUNTING STRUCTURE

As best illustrated in FIGS. 3 and 4, the rear housing portion 70, which contains the actuating means and the handle or trigger 79, is fabricated from two halves or pieces 140 and 142. In FIG. 3, a forward part of the rear housing piece 140 is broken away along the parting plane to show the other rear housing piece 142. As best illustrated in FIGS. 3 and 4, the housing pieces 140 and 142 are suitably secured together, as with screws, one of which screws 144 is visible in FIG. 4. These pieces 140 and 142 are preferably molded from the same materials as the housing front portion 60 described above.

Preferably the handle or trigger 79 is molded from the same material as the other housing pieces and is pivotably mounted to the rear housing portion 70 about a pivot shaft 150 as illustrated in FIGS. 3 and 10. To operate the trigger 79, the device 20 is typically grasped with the palm of the hand at the top of the rear housing portion 70 (as viewed in FIG. 3) with the fingers and/or thumb extending down to the trigger 79. The trigger 79 is operably connected with an actuating means, described hereinafter in detail, to move the flexible pusher member 74 from the retracted position (illustrated in FIG. 3) to the extended position (illustrated in FIG. 2b) wherein the fastener 30 is ejected from the discharge aperture of the needle 50.

FRONT AND REAR HOUSING ROTATION STRUCTURE

Figure 9:
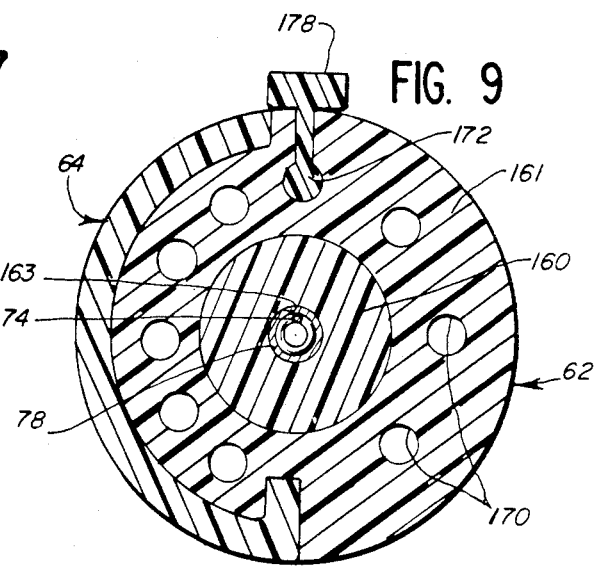
FIG. 9 is an enlarged, cross-sectional view taken generally along the plane 9—9 in FIG. 3.

As best illustrated in FIGS. 3 and 9, the rear housing piece 142 has a generally cylindrical portion 160 at the forward end of the rear housing. The front housing piece 62 has an annular portion or flange 161 in which the cylindrical portion 160 is received at the rear of the front housing piece 62. The cylindrical portion 160 has an aperture 163 through which the guide tube 78 passes. As best illustrated in FIGS. 3 and 4, the cylindrical portion 160 carries a spring clip or retaining ring means 164 in a groove for holding the cylindrical portion 160 within the flange 161 of the front housing piece 62. The ring 164 causes the rear housing pieces 140 and 142 to be biased forwardly with the cylindrical portion 160 until the rear housing pieces 140 and 142 engage the front housing pieces 62 and 64. This serves to hold together the rear housing 70 and front housing 60.

As best illustrated in FIG. 9, the annular portion 161 of the front housing piece 62 includes a plurality of circumferentially spaced cavities or bores 170 at selected azimuthal locations about the longitudinal axis of the instrument. These bores 170 are adapted to receive an engaging member or indexing pin 172 carried in a channel 174 of the rear housing piece 142. The channel 174 functions as a guide means for guiding the pin 172 for reciprocating movement into and out of one of the bores 170. The indexing pin 172 is biased forwardly into one of the bores 170 by means of a compression spring 176 which is disposed within the bore 174 between the end of the bore and the indexing pin 172.

The indexing pin has an upwardly extending member or button 178 adapted to be engaged by the thumb of the surgeon operating the fastener applier device 20. The button 178 has a T-shape when viewed from the side as in FIG. 3 and is connected to the pin 172 by a vertically extending stem portion. As best illustrated in FIG. 1, the button 178 is adapted to reciprocate within a channel 182 defined in the mating housing pieces 140 and 142. When the pin 172 is biased forwardly into one of the bores 170 by the spring 176 as illustrated in FIG. 3, the stem portion of the button 178 abuts the annular portion 161 and prevents further forward movement of the pin 172.

The front housing portion 60 and the rear housing portion 70 can be rotated relative to each other. Specifically, the front housing piece 62 together with the front housing piece 64 connected to the piece 62) can be rotated together relative to the rear housing portion 70 about the cylindrical portion 160 when the indexing pin 172 is pulled rearwardly out of engagement with the bores 170. When the desired orientation of the needle 50, relative to the trigger 79, is obtained, the indexing pin 172 is released by the surgeon. The indexing pin 172 is then forced forwardly by the spring 176 against the front housing piece 62. An additional slight rotation movement of the front housing portion 60, in either direction of rotation, may be necessary to align one of the bores 170 with the indexing pin 172, whereupon the indexing pin 172 is driven further forwardly by the spring 176 into a bore 170 to thereby lock the front housing portion 60 relative to the rear housing portion 70.

The housing rotation feature described above permits the needle, which extends from the front housing, to be positioned at a desired orientation relative to the rear housing by which the surgeon holds the device. This accommodates the application of fasteners to tissue in various parts of the body and reduces the possibility of the surgeon having to assume an awkward position relative to both the patient and device while operating the device.

ACTUATING MECHANISM

The rear housing portion 70 contains the novel actuating mechanism or means for reciprocating the flexible pusher member 74 between the retracted position and the extended position. The actuating mechanism is next described in detail with reference to FIGS. 10, 11 and 12 which illustrate the interior structure of the rear housing portion 70 of the fastener applier device.

FIGS. 10 and 11 show the rear housing piece 142 viewed along its parting plane with certain interior components illustrated in cross section. For ease of illustration in FIGS. 10 and 11, the front housing portion (portion 60 in FIG. 3) has not been shown and the indexing pin and its biasing spring (reference numerals 172 and 176, respectively, in FIG. 3) have likewise not been shown.

The housing piece 142 defines one-half of a first chamber 301 and one-half of a second chamber 302. As illustrated in FIG. 12, the other half of the rear housing, housing piece 140, defines the other halves of the first and second chambers 301 and 302, respectively. The chambers 301 and 302 are connected so that the interior volume of chamber 301 communicates with the interior volume of chamber 302.

The chambers 301 and 302 are generally cylindrical and are aligned or arranged on a common longitudinal axis. The first chamber 301 has a length greater than that of the second chamber 302. However, the diameter of the first chamber 301 is less than the diameter of the second chamber 302.

A first piston 321 is slidably disposed in the first chamber 301. The first piston 321 is provided with a pair of spaced-apart annular sealing rings or O-rings 323. A first piston biasing means or helical spring 324 is provided in the first chamber 301 between the first chamber 301 end wall 326 and the first piston 321. The first piston 321 is thus biased toward the second chamber 302 by the spring 324. The first piston 321 is adapted to be moved along chamber 301 between a first position illustrated in FIG. 10 and a second position illustrated in FIG. 11.

The end of the guide tube 78 is received in the first chamber end wall 326. The guide tube 78 projects forwardly beyond the end wall 326 away from the chamber 301 and into the front housing portion 60 wherein the guide tube 78 is arranged to guide the flexible pusher 74 into the channel 72 as described above with reference to FIG. 3. In the rear housing portion 70, the flexible pusher 74 extends from the guide tube 78, through an aperture in the chamber end wall 326, and into the first chamber 301 where it is secured to the piston 321.

As best illustrated in FIG. 10, a second piston 322 is slidably disposed within the second chamber 302. The second piston 322 has a pair of spaced-apart annular flanges 333 for sealingly engaging the cylindrical sidewall of the second chamber 302. A substantially incompressible fluid (not illustrated) is contained within the connected first and second chambers 301 and 302, respectively, between the first and second pistons 321 and 322, respectively. Preferably, the fluid is a sterile liquid, such as sterilized water.

Each piston 321 and 322 can be regarded as having a pressure bearing working surface that comprises the surface of the piston in contact with the fluid in the chambers. The working surfaces are not necessarily perpendicular to the longitudinal axis of the chambers, and hence, to the direction of movement of the pistons. The amount of force exerted by the piston on the fluid, or by the fluid upon the piston, is proportional to the projection area of the pressure bearing working surface of the piston normal to the direction of the piston movement. Preferably, as in the embodiment illustrated in FIGS. 10–12, the projection area of the pressure bearing working surface of the first piston 321 normal to the direction of the first piston movement is less than the projection area of the pressure bearing working surface of the second piston 322 normal to the direction of the second piston movement.

Further, the volume of the second chamber 302, as determined by the length of the stroke of the piston 322 within the second chamber 302, is equal to the volume of the first chamber 301 as determined by the length of the stroke of the first piston 321 in the first chamber 301. Consequently, movement of the second piston 322 (by means described in detail hereinafter) toward the first piston 321 will cause the first piston 321 to move from the first position (FIG. 10) along the length of the first chamber 301 until the volume of fluid discharged from the second chamber 302 has been received in the first chamber 301. At this point the first piston 321 is at the second position illustrated in FIG. 11. Since the diameter of the first chamber 301 is less than the diameter of the second chamber 302 as described above, the stroke of the first piston 301 between the first and second positions is necessarily greater than the corresponding stroke of the second piston 322. In this manner, the movement of the connected pusher member 74 is amplified relative to the movement of the second piston 322.

The second piston 322 is moved in the chamber 302 by the trigger 79 in cooperation with a novel mechanism. The second piston 322 carries a carries a cam follower 340 on a portion of the piston 322 that faces away from the piston pressure bearing working surface. Associated with the trigger or handle means 79 is an engaging means or arm 342 that is pivotally mounted to the rear housing 70 about a pin or shaft 344. The arm 342 defines an arcuate camming surface 343 which is engaged with the second piston cam follower 340.

As best illustrated in FIG. 12, the pin or shaft 344 is mounted at one end to a downwardly projecting tab 346 of the housing piece 142 and at the other end to a downwardly projecting tab 348 of the housing piece 140. The arm 342 is disposed on the shaft 344 between the tabs 346 and 348 and is adapted to pivot relative to the shaft 344 and relative to the housing pieces 140 and 142. The tabs 346, 348, the shaft 344, and the arm 342 are all enclosed by the hollow trigger or handle means 79.

As best illustrated in FIG. 10, the arm 342 defines a slot 350. The trigger or handle means 79 includes a handle pin 352 which is received in the slot. When the trigger 79 is in the unactuated position illustrated in FIG. 10, the pin 352 is at one end of the slot 350 in arm 342.

When it is desired to apply a fastener 30 with the device 20, the trigger or handle 79 is squeezed upwardly to a fully actuating position as illustrated in FIG. 11. This carries the handle pin 352 in the arm slot 350 to pivot the arm 342 in a first direction (counterclockwise as viewed in FIG. 11) with the camming surface 343 engaging the cam follower 340. This forces the second piston 322 along the second chamber 302 to force the hydraulic fluid into the first chamber 301. The first piston 321 is thus moved along the first chamber 301 (to the left as viewed in FIG. 7) and compresses spring 324. In this manner, the flexible pusher member 74 is moved through the housing of the device to eject a fastener 30 from the needle 50 as described above in detail with reference to FIGS. 1–9.

Preferably, a handle biasing means or spring 360 is provided to help pivot the handle 79 outwardly to an unactuated or handle releasing position. The spring 360 is wound around the handle of pivot shaft 150 and has a first end or loop 362 engaged with the first chamber end wall 326 and has a second end or loop 364 engaged with the handle.

Of course, depending upon the strength of the helical spring 324 behind the first piston 321, the spring 360 may not be required. If the spring 324 has a sufficiently high force, release of the trigger 79 by the surgeon will permit the spring 324 to drive the piston 321 to the end of the first chamber 301. This will cause the second piston 322 to be driven to the end of the second chamber 302 and to thereby pivot the arm 342 (in the clockwise direction as viewed in FIG. 10) to return the trigger 79 to the releasing position.

When the trigger 79 is released by the surgeon operating the fastener applier device 20, the first piston 321 returns to the beginning of its stroke and hence, the connected flexible pusher member 74 is returned to the retracted position wherein the leading end of the pusher member 74 is located behind the dispensing region to permit the next fastener 30 to be moved into the dispensing region in alignment with the needle 50 as described above with reference to FIGS. 1-9.

If desired, the diameter of the first piston 321 could be greater than the diameter of the second piston 322 so that the force of the operating member could be amplified relative to the force applied at the handle of the device.

Instead of providing sliding pistons with seals as illustrated for pistons 321 and 322, it may be desirable to provide chambers similar to chambers 301 and 302, but modified to include reciprocative sealed bellows structures at each end to function as pistons. This would provide a leak-tight design.

OTHER EMBODIMENTS

Although only one embodiment of the illustrated fastener applier device described herein has an actuating mechanism that includes hydraulic piston and cylinder operators, it is to be realized that any suitable actuating mechanism may be used with the fastener applier device, including a non-hydraulic actuating mechanism. The particular type of actuating mechanism, and the detailed structure of such an actuating mechanism, forms no part of the present invention.

From the foregoing, it will be observed that numerous variations and modifications may be effected without departing from the true spirit and scope of the novel concept of the invention. It is to be understood that no limitation with respect to the specific apparatus and method illustrated herein is intended or should be inferred. It is, of course, intended to cover by the appended claims all such modifications as fall within the scope of the claims.

What is claimed is:

1. In a device for closing a wound or incision in tissue with a plurality of fasteners, each said fastener being of the type comprising a filament member terminated on at least one end by an anchoring means, each said fastener being applied by said device to remain in the tissue with the filament member transversing the wound or incision through the tissue to maintain the tissue in approximation at the incision or wound, said device having a rear housing by which said device may be grasped, a front housing from which projects a hollow needle with a passage and slot extending along its length through which each said fastener is applied, a pusher member for pushing each said fastener along said needle, and means for moving said pusher member into and in said needle, the improvement characterized in that:

said hollow needle is oriented to extend laterally outwardly in a plane substantially normal to the length of said device, said needle having an entrance opening to said passage within said device, said needle having a distal end adapted for piercing said tissue, said needle being curved along at least a portion of its length to facilitate the picking up and holding of tissue as the tissue is pierced with the needle;

said pusher member is a flexible member slidably disposed within said housing;

guide means is provided in said front housing for guiding the movement of said flexible pusher member along a portion of said front housing and into alignment with the entrance opening of said hollow needle passage, said guide means being arranged to permit the positioning of each said fastener in a dispensing region adjacent the needle passage entrance opening and ahead of said flexible pusher member with said anchoring means in alignment with the entrance opening of said hollow needle passage;

said device includes a magazine means for retaining and guiding a plurality of said fasteners in side-by-side relationship, said magazine means including biasing means for biasing said plurality of fasteners toward said dispensing region whereby said anchoring means of one of said fasteners is positioned in said dispensing region ahead of said flexible pusher member and in alignment with the entrance opening of said hollow needle passage; and said means for moving said pusher member into and in said needle includes means carried by said rear housing for moving said flexible pusher member from a retracted position wherein the pusher member is spaced behind the dispensing region to permit an anchoring means of one of said fasteners to be moved into the dispensing region in alignment with the entrance opening of said needle passage to an extended position wherein said flexible pusher member ejects the fastener from said needle.

2. The improvement in accordance with claim 1 in which said needle has a curvature defined along the locus of a circular arc.

3. The improvement in accordance with claim 1 in which said front housing is mounted for rotatior relative to said rear housing.

4. In a device for closing a wound or incision in tissue with a plurality of fasteners, each said fastener being of the type comprising a filament member terminated on at least one end by an anchoring means, each said fastener being applied by said device to remain in the tissue with the filament member transversing the wound or incision through the tissue to maintain the tissue in approximation at the wound or incision, said device comprising at least one elongate housing, a hollow needle having a passage and slot extending along its length through which each said fastener is applied, a pusher member for pushing each said fastener along said needle, and means for moving said pusher member into said needle and out of an end of said needle, the improvement characterized in that:

said hollow needle is oriented to extend laterally outwardly in a plane substantially normal to the length of said device, said needle having an entrance opening to said passage within said housing, said needle having a distal end adapted for piercing said tissue, said needle being curved along at least a portion of its length to facilitate the picking up and holding of tissue as the tissue is pierced with the needle; and said pusher member is an elongate flexible member disposed within said housing in an arcuate path and is adapted to be moved between a retracted position spaced rearwardly of said curved needle and an extended position wherein said flexible pusher member is slidably received in said curved needle.

5. The improvement in accordance with claim 4 in which said needle curvature is a circular arc.

6. The improvement in accordance with claim 5 in which said needle passage opens inwardly through said slot toward the center of curvature of the needle.

7. The improvement in accordance with claim 4 in which said hollow needle extends laterally from a front portion of said housing in a plane normal to the length of the housing.

8. The improvement in accordance with claim 4 in which said device has a front housing and a rear housing, in which said needle projects from said front housing, in which said device is adopted to be grasped by said rear housing, and in which said front and rear housings are mounted together end-to-end for relative rotation about a common longitudinal axis that is normal to the plane in which said needle extends from said housing.

9. In a device for closing a wound or incision in tissue with a plurality of fasteners, each said fastener being of the type comprising a filament member terminated on at least one end by an anchoring means, each said fastener being applied by said device to remain in the tissue with the filament member transversing the wound or incision through the tissue to maintain the tissue in approximation at the wound or incision, said device comprising at least one elongate front housing portion, a hollow heedle having a passage and slot extending along its length through which each said fastener is applied, a pusher member for pushing each said fastener along said needle, and means for moving said pusher member into and out of an end of said needle, the improvement characterized in that:

said hollow needle is carried by and extends laterally from said front housing portion, said needle is oriented to extend laterally outwardly relative to the length of said device, said needle has an entrance opening to said passage within said housing, said needle has a distal end adapted for piercing said tissue, said needle is curved in a circular arc along the entire portion of its length that extends laterally beyond said front housing to facilitate the picking up and holding of tissue as the tissue is pierced with the needle; and said pusher member is an elongate flexible member disposed within said housing in an arcuate path and is adapted to be moved between a retracted position spaced rearwardly of said curved needle and an extended position wherein said flexible pusher member is slidably received in said curved needle.

10. In a device for closing a wound or incision in tissue with a plurality of fasteners, each said fastener being of the type comprising a filament member terminated on at least one end by an anchoring means, each said fastener being applied by said device to remain in the tissue with the filament member transversing the wound or incision through the tissue to maintain the tissue in approximation at the wound or incision, said device comprising at least a hollow needle having a passage and slot extending along its length through which each said fastener is applied, a pusher member for pushing each said fastener along said needle, and means for moving said pusher member into said needle, the improvement characterized in that:

said device has a front housing and a rear housing that are mounted together end-to-end for relative rotation about a common longitudinal axis to selected relative orientations; and said needle is carried by and extends from said front housing.

* * * * *